US006889923B2

(12) United States Patent
Gutierrez et al.

(10) Patent No.: US 6,889,923 B2
(45) Date of Patent: May 10, 2005

(54) POWDER PROCESSING

(75) Inventors: Emilio J Gutierrez, New York, NY (US); Peter M. Hafermann, Yorba Linda, CA (US); Matthew W. Phillips, Tustin, CA (US)

(73) Assignee: Botanicals International, Long Beach, CA (US)

( * ) Notice: Subject to any disclaimer, the term of this patent is extended or adjusted under 35 U.S.C. 154(b) by 403 days.

(21) Appl. No.: 09/836,003

(22) Filed: Apr. 17, 2001

(65) Prior Publication Data

US 2001/0019763 A1 Sep. 6, 2001

Related U.S. Application Data

(62) Division of application No. 09/239,104, filed on Jan. 28, 1999, now Pat. No. 6,276,917.

(51) Int. Cl.[7] .............................................. B02C 19/12
(52) U.S. Cl. ............................................. 241/3; 241/29
(58) Field of Search ....................... 241/3, 29; 264/118; 425/237, 331, 352

(56) References Cited

U.S. PATENT DOCUMENTS

| 4,072,535 A | * | 2/1978 | Short et al. ............... 106/206.1 |
| 5,041,410 A | * | 8/1991 | Ivie ............................ 502/401 |
| 5,207,389 A | * | 5/1993 | Hall et al. ....................... 241/3 |
| 5,229,348 A | * | 7/1993 | Ivie ............................ 502/401 |
| 5,598,770 A | * | 2/1997 | Campbell et al. ............. 99/487 |

* cited by examiner

Primary Examiner—Mark Rosenbaum
(74) Attorney, Agent, or Firm—Charles Berman, Esq.; Enrica Bruno, Esq.

(57) ABSTRACT

A system is provided for pelletizing particulate raw matter having a first density, and thereafter subjecting the pellets to a milling process to obtain a powdered form of the particulate. During pelletizing steam can be added. The resulting powder is denser, or more granular or has better flow with less dust than the pre-pelletized particulate matter having the first density. The powderized particulate has applications for pharmaceutical, nutritional and herbal end products.

29 Claims, 2 Drawing Sheets

POWDER PROCESSING

CROSS REFERENCE TO RELATED APPLICATIONS

This application is a divisional of U.S. application Ser. No. 09/239,104 filed Jan. 28, 1999, issued as U.S. Pat. No. 6,276,917 on Aug. 21, 2001.

BACKGROUND OF THE INVENTION

This invention relates to forming particulate powderized materials for use, particularly in the pharmaceutical, nutritional and dietary supplement industries. The invention is particularly concerned with providing an end product, which is denser, more granular and generates less dust with better flow than previously known products for these purposes. This is particularly valuable in that the end product has a minimum of, and in most cases no, fillers or diluents to obtain the desired end product, which is therefore substantially pure.

Traditional densification and dry granulation is performed mainly by the pharmaceutical industry using a roll compactor. An example of this is system known as the Chilsonator™. The success of roll compaction is limited by the compactability or cohesiveness of the specific material. Frequently, the material requires preblending with compressible fillers and diluents in order to achieve compaction. Even with the most suitable fillers, roll compaction is frequently inefficient and slow because not all of the material gets compacted on the first pass through the rollers. Uncompacted material must be constantly recycled back through the machine until compacted. Compacted material forms a thin brittle ribbon which is then ground back into a powder of desired particle size. The resulting powder is normally higher in density or more compressible. The resulting powder however has fillers or diluents, which are generally undesirable.

An alternate way of accomplishing similar results is by using a tablet press to compress large tablets or slugs ("slugging") then milling them back into a powder. This format also has the disadvantage that there are diluents and fillers, which are generally undesirable.

There is, accordingly, a need to provide for improved system of powderized products which can provide enhanced flow properties, and better compaction and compressibility. There is a need to provide such a system which can permit for the production of end products, for instance, in the form bulk powders, or powders for tableting or encapsulating in gelatin capsules or the like.

SUMMARY OF THE INVENTION

By this invention the Applicants minimize the disadvantages of known techniques for processing raw material products. The Applicants provide a system for forming powderized or granulated products of higher density, with less dust, better granularity and better flow characteristics.

According to the invention, there is a system as provided for pelletizing particulate raw matter, and thereafter subjecting the pellets to a milling process to obtain a powdered form of the particulate. During pelletizing steam can be added. The resulting powder is denser, more granular and has better free flow properties than the pre-pelletized particulate matter. The powderized particulate has applications for pharmaceutical, nutritional and dietary supplement end products.

A system is provided for pelletizing particulate raw matter having a first density, and thereafter subjecting the pellets to a milling process to obtain a powdered form of the particulate. During pelletizing steam can be added. The resulting powder is denser, more granular and has better flow than the pre-pelletized particulate matter having the first density. The powderized particulate has applications for pharmaceutical, nutritional and dietary supplement finished products.

Apparatus for processing products for increasing the density of particulate matter in a powderized form comprises feed means for directing particulate matter into a pelletizing mill, the particulate matter being in a first powderized form and having a first density. A pelletizing mill generates pellets of the particulate matter. The pellets are then milled into a second powderized form, whereby the second powderized form of the particulate has a greater density than the first density. This is achieved in a manner where the formed pellet substantially exclude diluents or fillers.

During pellitization, some products required the introduction of saturated steam at a selected temperature, pressure and condensation characteristic. There is at least about 95% substantially pure saturated steam under a pressure of about 40 to about 80 PSI at about a temperature of about 180° F. to about 400° F. This hydrates the particulate matter at a temperature of about 80° F. to 200° F. and thereby add about 1% moisture to the particulate matter. The product with increased moisture content is forced under pressure through a spinning perforated dye of a predetermined dimension thereby to obtain a pellet of a selected size, the forcing through the dye being effected selectively by dual inner rotating roller means.

There is a pre-milling step for processing raw materials to obtain a particulate matter for feeding into the pelletizing mill. The pellets exposed to steam are cooled to a substantially ambient temperature prior to being milled. A cooler at an outlet from the pelletizing mill permits ambient air to pass through a bed containing pellets discharged from the pelletizing mill.

The processed product is relatively coarser, capable of improved flow and relatively more compressible than the particulate matter. The powderized product in the second form has relatively greater granularity than the particulate matter in the first form In the second powderized form the product can be made into, selectively, bulk powders such as teas or sports drinks or tablets, and capsules, and selectively have at least one other ingredient.

The invention is further described with reference to the accompanying drawings.

BRIEF DESCRIPTION OF THE DESCRIPTION DRAWINGS

DETAILED DESCRIPTION OF THE PREFERRED EMBODIMENT

Figure 1:
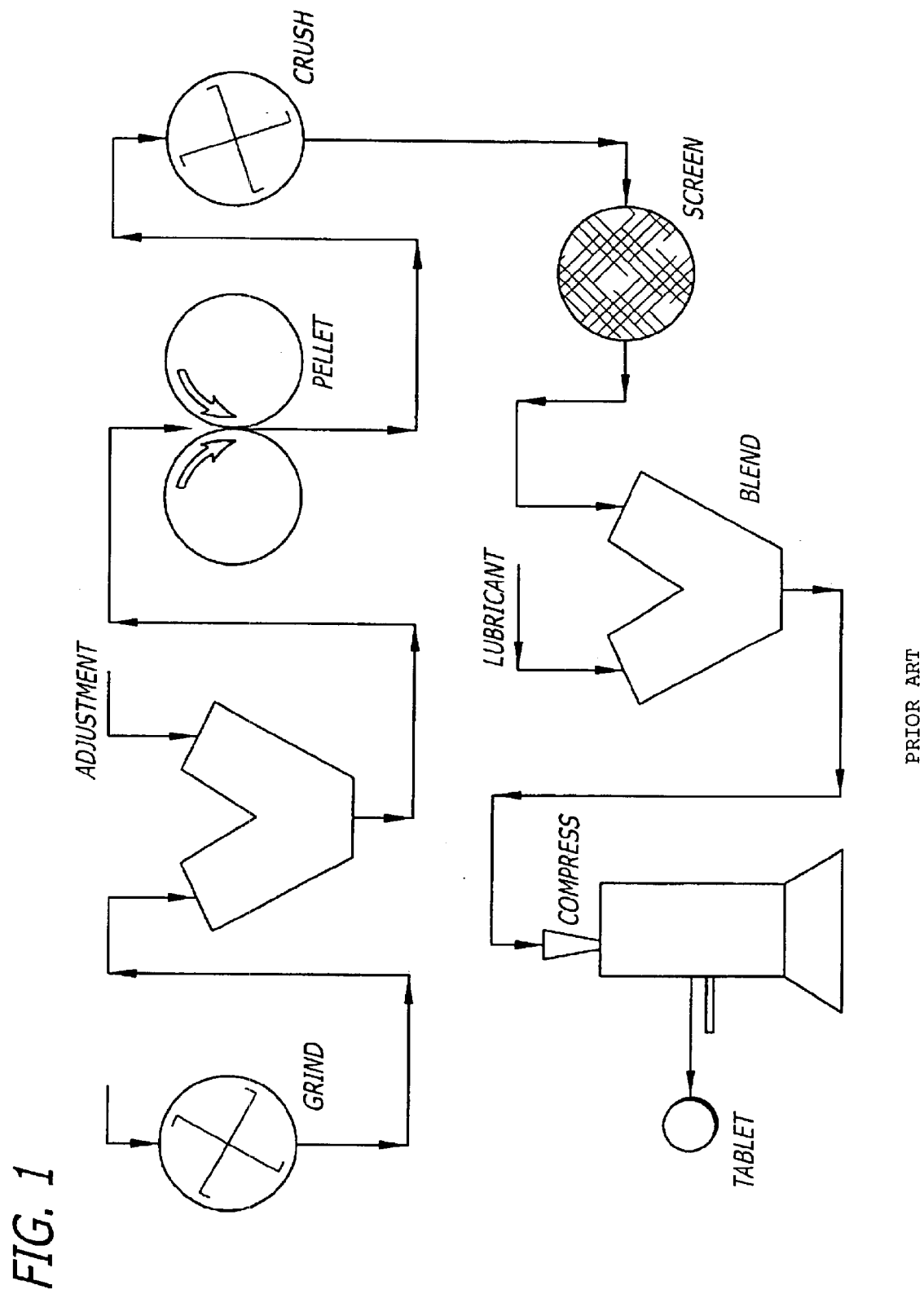
FIG. 1 is a flow diagram illustrating a prior art method to form granular materials and tablets according to a dry granulation technique.
Figure 2:
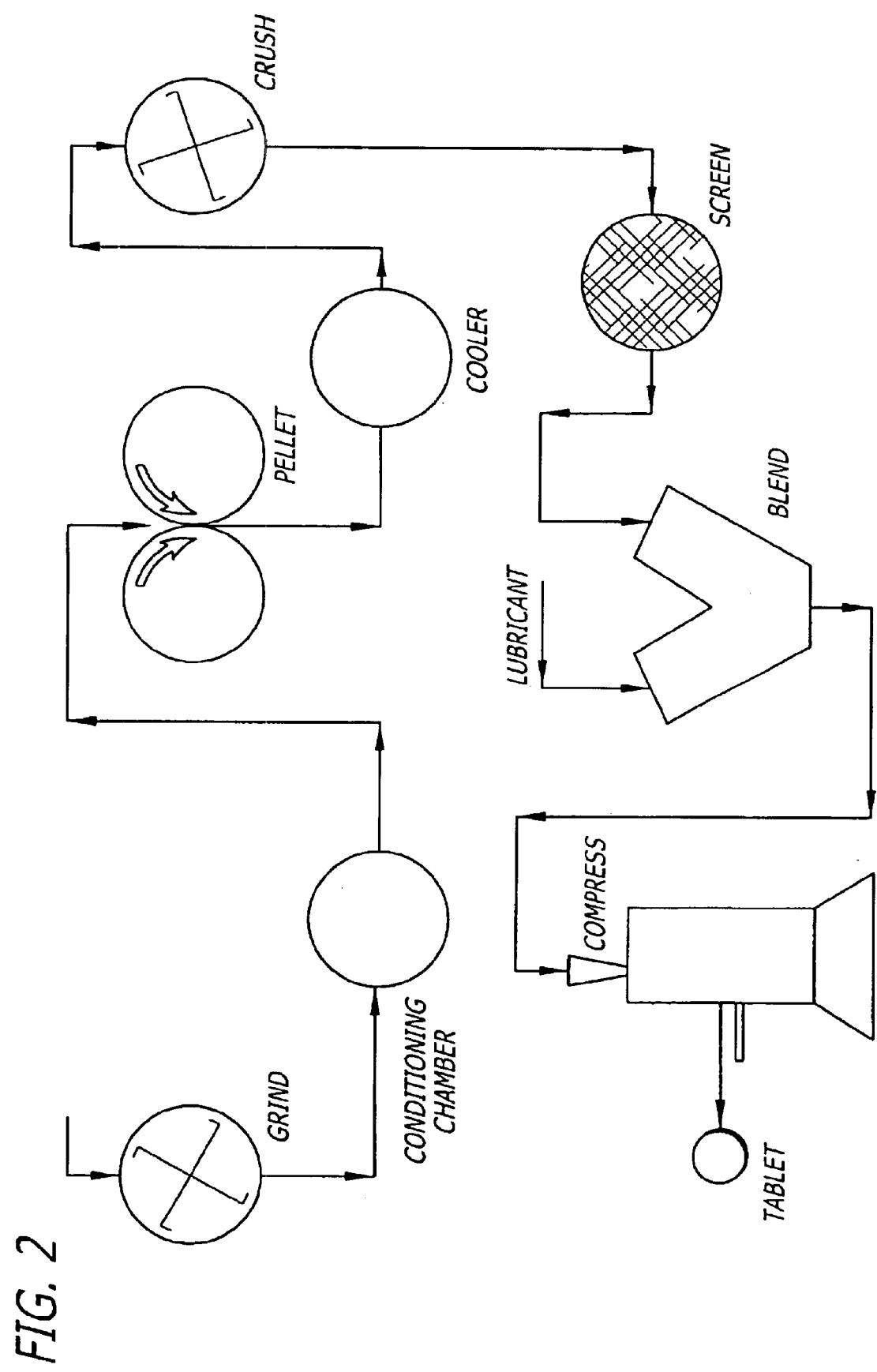
FIG. 2 is a flow diagram illustrating a method to form granular materials and tablets according to a dry granulation system of the invention.

The Applicants describe by example a system, apparatus and method for performing the process of the invention. The invention includes the apparatus for performing the process under the process and also products made by the apparatus.

The system provides for pelletizing particulate raw matter, and thereafter subjecting the pellets to a milling process to obtain a powdered form of the particulate. During pelletizing steam is added. The resulting powder is denser, more granular and has better flow than the pre-pelletized particulate matter. The powderized particulate end product has applications for pharmaceutical, nutritional and herbal end products.

There is apparatus and a method for processing products for increasing the density of particulars in a powderized form. Feed means directs particulate matter into a pelletizing mill. The particulate matter has a first density. The pelletizing mill forms pellets of the particulate matter. Thereafter the pellets are milled into a powderized form. The powderized form of the particulate has a second density which is a greater density than the first density.

The steam fed pellet mill is used to increase the density of powders, create or enlarge granules, control particle size, enhance flow properties, decrease dust and create granulations without using diluents or fillers. The products are particularly, but not exclusively, applicable to making end products for the pharmaceutical, nutritional or dietary supplement industries.

General Description of Pelletizing Process:

A pellet mill originally designed to make animal feed is used to control particle size, increase a product's density, or add granularity and decrease dust by forming a pellet and milling it back into powder form.

Particulate product of predetermined particle size is fed into a conditioning chamber where it can be exposed to saturated steam of controlled temperature, pressure and condensation. The steam increases the product's inherent moisture content and compressibility. This benefit is normally only obtained through the use of compressible fillers in the traditional dry granulation methods of the pharmaceutical industry.

To form the pellet, the conditioned product is forced at extreme pressure through a spinning perforated die of preselected dimension by two rotating inner rollers. Nearly all of the material compresses into pellets with a minimal amount of product "fines". The lack of "fines" increases the pellet mill's overall output because there is no need to recycle a large percentage of the product back through the machine. Increased product throughput with minimal recycling makes pelletizing much more cost effective than alternate dry granulation means.

Pellets are quickly cooled to room temperature and milled to a specific particle size range based on the intended application of the product. The resulting powder is coarser, denser, better flowing with less dust, and more compressible or compactable. This makes it ideal for the manufacturing of pharmaceutical dosage forms such as tablets and capsules or nutritional powder drink mixes. This can be a powder blend.

Pre-Milling—(Preparing the Raw Material for Pelletizing)

Using a hammermill or equivalent milling device for whole plants, roots, leaves, dried fruits or pharmaceutical actives are ground to produce a fine homogeneous powder. Traditionally, the pellet mill is used to manufacture products for the grain or animal feed industry. In this prior art application, molasses, starches and fats are added at the conditioning chamber along with steam to help the material bind together. Required particle size is only about 700 microns (25 mesh) because the binders help hold the pellet together.

Binders used to make animal feed are not desirable in the pelletizing of herbal or pharmaceutical products according to the present invention. Without binders, the particle size of the starting raw material becomes extremely critical. Products are ground to finer particle size, ranging from 100 to 1300 microns (14 to 150 mesh), to increase the surface area and create more binding sites within each individual particle. The compacting step requires more shear force because it is dependent on steam or the product's own compressible properties.

Steam and the Conditioning Chamber

Inside the conditioning chamber, the powder bed is typically penetrated by 95% to 100% pure saturated steam with a typical pressure of 40 to 80 PSI. Steam temperature may range between 180° F. to 400° F. while it heats and hydrates the powder to a temperature of 80° F. to 200° F. adding approximately 1% moisture. Products that are naturally compressible solely by shear force, require no steam to form a pellet.

Feeding the Pellet Mill

The rate at which the conditioning chamber feeds the pellet mill is controlled by the amount of steam and the required heat exposure to form good pellets. Feeding rate is also controlled by resistance created inside the die while pelletizing, product flow and force needed to compress. Ultimately, an optimum flow rate setting is determined for each individual product.

The Effect of Product Variability on the Pelletizing Process

Certain products with good compressible properties such as ginger root powder can be pelletized with little or no steam depending on the individual product lot.

Products which contain a high percentage of fibrous matter, such as Siberian Ginseng, require substantial exposure to steam and greater force to compact.

Products with low melting points that compact with minimal force require a relieved die that subjects the product to less shear force and friction. These products will also form pellets without the need for steam.

Characteristics of a Typical Pellet Mill

25HP Motor 1800 RPM
   Die Speed 230 RPM
   Mixer Speed 500 RPM
   12' die, standard, 3.94" wide 149 $in^2$ Working Area
   Density of typical pellet 1.3 g/mL
   Length of pellets can vary between ¼" to 2" depending on the blade setting
   CPM (California Pellet Mills), Series 1100 Pellet Mill or Series 3000 Pellet Mill with Counter flow Coolers.

Cooler

Heated pellets are discharged from the pellet mill into the cooler. The cooler fan draws ambient air upward through the pellet bed. The pellets are cooled gradually as they move through the rising air current. To prevent cooling shock, cold air comes in contact with cooled hardened pellets while incoming hot pellets come in contact with air preheated by the warm pellets before it.

Specification in Milling Pellets—Controlling Particle Size and Density

Pellets are milled to meet a wide range of specifications. Typical ranges can be anywhere between 100 and 1300 microns or 100% through 14 to 150 mesh.

For raw materials that are going to be compresses into tablets, a normal requirement would be 100% through a 14 mesh with a bell shape standard distribution of particle sizes and perhaps no more than 40% through a 100 mesh. This would be difficult to produce without the pelletizing process because most raw material powders would be either too fine or of a homogeneous particle size. The granularity created by the pelletizing process is what makes the product suitable for tablet compression.

For raw materials that are going to be placed inside gelatin capsules, a typical particle size requirement can be 100% through a 60 or 80 mesh. Powders that are just milled and do not undergo the pelletizing process can sometimes be as fine as 100% through 200 mesh. These products are dusty and difficult to work with because of their poor flow characteristics. The pelletizing process would make this product coarser and better flowing.

Added density and no fillers allow product formulators design dosage forms with more consumer appeal. Tablets and capsules are smaller, more concentrated or undiluted and easier to swallow.

Advantages

Particle size shift to bigger screens on the sieve analysis test—more coarse particles result and less dust or fines.

Better particle size distribution—not all particles are nearly the same size.

Same moisture—Steam does not add additional moisture to the final product.

Increased density—Density increase in excess of 100% is possible on some products.

Increased fill weight on gelatin capsules—More product fits in a small capsule.

Better flow—Less tablet or capsule weight variability through better flow and compactability.

More granularity—Some products are now compressible without compressible fillers.

Increased manufacturing efficiency—Pellet mill offers more product throughput than traditional means of the pharmaceutical industry.

Applicants now set out in Table 1 some example products as illustrated. For each of these raw material products, there is set out the normal powder characteristics and also the pelletized powder characteristics, the latter being in terms of the current invention.

TABLE 1

HD Powder Line Example Products

| | Density | Loose | % Gain | Tapped | % Gain | Mesh Size |
|---|---|---|---|---|---|---|
| Ginkgo | Normal Powder | 0.29 | | 0.43 | | |
| Leaf HD | Pelletized Powder | 0.43 | 48% | 0.56 | 30% | 60 |
| Korean | Normal Powder | 0.44 | | 0.59 | | |
| Ginseng Root HD | Pelletized Powder | 0.56 | 27% | 0.75 | 27% | 60 |
| Echinacea | Normal Powder | 0.22 | | 0.40 | | |
| Purpurea Herb HD | Pelletized Powder | 0.50 | 127% | 0.70 | 75% | 60 |
| Gota Kola | Normal Powder | 0.35 | | 0.50 | | |
| Herb HD | Pelletized Powder | 0.56 | 60% | 0.80 | 60% | 60 |
| Valerian | Normal Powder | 0.47 | | 0.62 | | |
| Officinalis Root HD | Pelletized Powder | 0.64 | 36% | 0.80 | 29% | 40 |
| Siberian | Normal Powder | 0.45 | | 0.61 | | |
| Ginseng Root HD | Pelletized Powder | 0.68 | 51% | 0.90 | 48% | 60 |
| Feverfew | Normal Powder | 0.28 | | 0.41 | | |
| Herb HD | Pelletized Powder | 0.53 | 89% | 0.70 | 71% | 40 |
| Astragalus | Normal Powder | 0.36 | | 0.57 | | |
| Root HD | Pelletized Powder | 0.57 | 58% | 0.77 | 35% | 40 |
| Red | Normal Powder | 0.31 | | 0.49 | | |
| Raspberry Leaves HD | Pelletized Powder | 0.38 | 23% | 0.56 | 14% | 80 |
| Foti | Normal Powder | 0.49 | | 0.62 | | |
| Root HD | Pelletized Powder | 0.66 | 35% | 0.80 | 29% | 40 |
| Alfalfa | Normal Powder | 0.19 | | 0.34 | | |
| Herb HD | Pelletized Powder | 0.43 | 126% | 0.53 | 56% | 40 |
| Ginger | Normal Powder | 0.41 | | 0.61 | | |
| Root HD | Pelletized Powder | 0.54 | 32% | 0.75 | 23% | 20 |
| Black | Normal Powder | 0.55 | | 0.58 | | |

TABLE 1-continued

HD Powder Line Example Products

| | Density | Loose | % Gain | Tapped | % Gain | Mesh Size |
|---|---|---|---|---|---|---|
| Cohosh Root HD | Pelletized Powder | 0.61 | 11% | 0.73 | 26% | 40 |
| Cat's | Normal Powder | 0.40 | | 0.58 | | |
| Claw Root HD | Pelletized Powder | 0.54 | 35% | 0.70 | 21% | 60 |
| Nettle | Normal Powder | 0.35 | | 0.48 | | |
| Root HD | Pelletized Powder | 0.52 | 49% | 0.66 | 38% | 80 |
| St. John's | Normal Powder | 0.34 | | 0.42 | | |
| Wort Herb HD | Pelletized Powder | 0.48 | 41% | 0.52 | 24% | 40 |
| Echinacea | Normal Powder | 0.25 | | 0.33 | | |
| Angustifolla Root HD | Pelletized Powder | 0.49 | 96% | 0.57 | 73% | 40 |
| Red | Normal Powder | 0.30 | | 0.43 | | |
| Clover Tops HD | Pelletized Powder | 0.36 | 20% | 0.52 | 21% | 80 |

The Applicants further set out other exemplary data showing the effectiveness of the product in terms of the invention.

In Table 2 a prior art normal powder technique is set out with its effective analysis. The comparative table for the same product is set out in terms of the present invention in Table 4. Compare the sections labeled Sieve Analysis and Tapped Density.

In Table 3 sets out a normal powder analysis for a different product in terms of the prior art. Table 5 sets out an analysis of the same product in terms of the invention. Also, compare the sections labeled Sieve Analysis and Tapped Density.

TABLE 2

Normal Powder (Prior Art)
SIEVE ANALYSIS

| Test Description | | Result |
|---|---|---|
| % THROUGH US | #40 SCREEN | 100.0000 |
| % THROUGH US | #60 SCREEN | 98.5000 |
| % THROUGH US | #80 SCREEN | 58.9000 |
| % THROUGH US | #100 SCREEN | 48.3000 |
| % THROUGH US | #140 SCREEN | 33.6000 |

TABLE 3

Normal Powder (Prior Art)
SIEVE ANALYSIS

| Test Description | | Result |
|---|---|---|
| % THROUGH US | #40 SCREEN | 100.0000 |
| % THROUGH US | #60 SCREEN | 99.8000 |
| % THROUGH US | #80 SCREEN | 85.0000 |
| % THROUGH US | #100 SCREEN | 74.5000 |
| % THROUGH US | #140 SCREEN | 56.0000 |

TABLE 4

Pelletized Powder (Invention)
SIEVE ANALYSIS

| Test Description | | Result |
|---|---|---|
| % THROUGH US | #40 SCREEN | 100.0000 |
| % THROUGH US | #60 SCREEN | 99.3000 |
| % THROUGH US | #80 SCREEN | 68.3000 |
| % THROUGH US | #100 SCREEN | 55.0000 |
| % THROUGH US | #140 SCREEN | 30.9000 |

TABLE 5

Pelletized Powder (Invention)
SIEVE ANALYSIS

| Test Description | | Result |
|---|---|---|
| % THROUGH US | #40 SCREEN | 100.0000 |
| % THROUGH US | #60 SCREEN | 98.1000 |
| % THROUGH US | #80 SCREEN | 70.7000 |
| % THROUGH US | #100 SCREEN | 58.2000 |
| % THROUGH US | #140 SCREEN | 37.3000 |

Many other forms of the invention exist, each differing from the other in matters of detail only. For instance different feed means can be used for directing particulate matter into the pelletizing mill. Different consistencies of the particulate matter in its first powderized form and first density are possible. Different formats of pelletization are possible. Different pellet mill manufacturers and different pellet mill sizes and die specifications are possible.

Although ideally there are no diluents or fillers, it is possible under certain preferred formulations to add a degree of such products. The introduction of steam into the pellet mill may be optional, as indeed are different pressures and temperatures possible. Cooling of the pellets to a substantially ambient temperature prior to being milled by the milling means can be optional. Other cooling temperatures are possible.

The increased moisture content can be added by techniques other than forced pressure through a spinning perforated dye, and other than by forcing material through the dye being effected selectively by inner rotating roller means. The pellets can vary in size, consistency and shape. The milled pellets output in a powderized form can have sizes different to a size between about 100 to about 800 microns. Also, the size of the output powder can be different to a size where about 100% of the powderized product is passable through a 14 mesh.

The end products of the method and/or apparatus may be for use in industries other than for the pharmaceutical, nutritional or herbal end products.

The invention is to be determined solely by the following claims.

What is claimed is:

1. A process for producing products in a powderized form comprising:
   directing particulate matter into a pellet mill, the particulate matter selected from the grow consisting of particulate matter of whole plants, leaves, roots, dried fruits and active pharmaceuticals, the particulate matter being in a first powderized form and having a first density;
   generating pellets of the particulate matter in substantial absence of fillers, diluents or binders; and
   milling the pellets into a second powderized form, whereby the second powderized form of the particulate has a greater density than the first density.

2. A process as claimed in claim 1 including introducing hydration into the pellet mill during formation of pellets.

3. A process as claimed in claim 1 including ensuring that the particulate matter includes material for at least one of pharmaceutical, nutritional or herbal end product.

4. A process as claimed in claim 1 including applying hydration at a selected temperature and pressure and condensation characteristic to the pellet mill during pelletization thereby to increase the moisture content of the product.

5. A process as claimed in claim 4 including ensuring that the product with increased moisture content is forced under pressure through a spinning perforated die of a predetermined dimension thereby to obtain a pellet of a selected size, and means for effecting the forcing through the die being effected selectively by rotating inner roller means.

6. A process as claimed in claim 5 including cooling the pellets to a substantially ambient temperature prior to being milled by the milling means.

7. A process as claimed in claim 1 including pro-milling for processing raw materials to obtain a particulate matter for feeding into the pellet mill.

8. A process as claimed in claim 1 including ensuring that the size of a particulate in the first form is greater than about 150 microns.

9. A process as claimed in claim 1 including conditioning the particulate material in a conditioning chamber at at least about 95% hydration under a pressure of about 40 to about 80 PSI thereby to hydrate the particulate matter and thereby add about 1% moisture to the particulate matter.

10. A process as claimed in claim 9 including cooling an outlet from a pellet mill for permitting ambient air to pass through a bed containing pellets discharged from the pelletizing mill.

11. A process as claimed in claim 1 including ensuring that the milled pellets output in a powderized form has an approximate size between about 100 to about 1300 microns, or of a size where essentially most of the powderized product is between a 14 mesh to a 150 mesh.

12. A process as claimed in claim 1 including ensuring that the powderized form of the milled product has a particle size permitting about 100% passage through a 60 to 80 mesh.

13. A process for producing pharmaceutical, nutritional or herbal end powdered product, wherein the density of the pharmaceutical nutritional or herbal powdered and product in a powderized form is increased comprising:
   directing particulate matter that constitute a pharmaceutical nutritional or herbal powdered end product into a pellet mill, the particulate matter selected from the group consisting of particulate matter of whole plants, leaves, roots, dried fruits and active pharmaceuticals, the particulate matter being in a first powderized form and having a first density;
   generating pellets of the particulate matter for constituting the pharmaceutical, nutritional or herbal powdered end product in substantial absence of fillers, diluents or binders; and
   milling the pellets into a second powderized firm whereby the second powderized form of the particulate for constituting the pharmaceutical, nutritional or herbal powdered end product has a greater density than the first density.

14. A process as claimed in claim 13 including applying hydration at a selected temperature and pressure and condensation characteristic to the pellet mill during pelletization thereby to increase the moisture content of the product.

15. A process as claimed in claim 14 including ensuring that the product with increased moisture content is forced under pressure thought a spinning perforated die of a predetermined dimension thereby to obtain a pellet of a selected size, and means for effecting the forcing tough the die being effected selectively by rotating inner roller means.

16. A process as claimed in claim 15 including cooling the pellets to a substantially ambient temperature prior to being milled.

17. A process as claimed in claim 13 including pre-milling for processing raw materials to obtain a particulate matter for feeding into the pellet mill.

18. A process as claimed in claim 13 including ensuring that the size of particulate in the first form is greater than about 150 microns.

19. A process as claimed in claim 13 including conditioning the product at at least 95% hydrates under a pressure o about 40 to about 80 PSI thereby to hydrate the particulate matter and thereby add about 1% moisture to the particulate matter.

20. A process as claimed in claim 19 including cooling at an outlet from the pelletizing mill for permitting ambient air to pass though a bed containing pellets discharged from the pellet mill.

21. A process as claimed in claim 13 including ensuring that the milled pellets output has an approximate size between about 100 to about 1300 microns, or of a size where essentially most of the product is between a 14 mesh to a 150 mesh.

22. A process as claimed in claim 13 including ensuring that the powderized form of the milled product has a particle size permitting about 100% passage through a 60 to 80 mesh.

23. A process for forming a pharmaceutical, nutritional or herbal powderized end product wherein the density of pharmaceutical, nutritional or herbal powderized end product in a powderized form is increased comprising:

directing particulate matter to constitute a pharmaceutical, nutritional or herbal powderized end product into a pelletizing mill, the particulate matter selected from the group consisting of particulate matter of whole plants, leaves, roots, dried fruits and active pharmaceuticals, the particulate matter being in a first powderized form and having a first density;

generating pellets of the particulate matter for constituting the pharmaceutical nutritional herbal end product in substantial absence of fillers, diluents or binders; and milling the pellets into a second powderized form for the pharmaceutical, nutritional or herbal powderized end product, the second powderized form having a second density greater than the first density, to provide a pharmaceutical, nutritional or herbal powderized end product having a density greater than at least from about 14% to about 40% relative to a pharmaceutical, nutritional or herbal powderized end product where said pellets are generated in presence of the fillers diluents or binders.

24. A process for producing a product in a powderized form comprising:

directing particulate matter into a pellet mill, the particulate matter selected from the group consisting of particulate matter of whole plants, leaves, roots, dried fruits and active pharmaceuticals, the particulate matter being in a first powderized form and having a first granularity;

generating pellets of the particulate matter in substantial absence of fillers, diluents or binders; and milling the pellets into a second powderized form, whereby the second powderized form of the particulate matter has a greater granularity than the first granularity.

25. The process of claim 24, wherein the particulate matter of whole plant, root, leaf and dried fruit, is particulate matter from a plant selected from the group consisting of *Ginko*, Korean ginseng, *Echinacea purpurea*, Gota Kola, *Valerian Officinalis*, Siberian ginseng, Feverfew, *Astragalus*, Red Raspeberry, Foti, Alfalfa, Ginger, Black Cohosh, Cat's Claw, Nettle, St John Wort, *Echinacea Angustifolia* and Red Clover.

26. The process of claim 24, wherein the particulate matter is selected from the group consisting of Gingko leaf, Korean Ginseng root, Echinacea Purpurea herb, Gota kola herb, Valerian Officioslis root, Siberian Ginseng root, Feverfew herb, astragalus root, Red Raspberry leaf; Foti root, Alfalfa herb, Ginger root, Black Cohosh root, Cat's claw root, Nettle root, St. John Wart herb, Echinacea Angustifolia root and Red Clover tops.

27. A process for producing a product in a powderized form comprising:

directing particulate matter into a pellet mill, the particulate matter selected from the group consisting of particulate matter of whole plants, leaves, roots, dried fruits and active pharmaceuticals, the particulate matter being in a first powderized form and baying a first flowability generating pellets of the particulate matter in substantial absence of fillers, diluents or binders; and milling the pellets into a second powderized form, whereby the second powderized form of the particulate matter has a greater flowability than the first flowability.

28. The process of claim 27, wherein the particulate matter of whole plant, root, leaf and dried fruit, is particulate matter from a plant selected from the group consisting of *Ginko*, Korean ginseng, *Echinacea purpurca*, Gota Kola, *Valerian Officinalis*, Siberian ginseng, Feverfew, *Astragalus*, Red Raspeberry, Foti, Alfalfa, Ginger, Blank Cohosh, Cat's Claw, Nettle, St John Wort, *Echinacea Angustifolia* and Red Clover.

29. The process of claim 27, wherein the particulate matter is selected from the group consisting of Gingko leaf; Korean Ginseng root, Echinacea Purpurea herb, Gota kola herb, Valerian Officinalis root, Siberian Ginseng root, Feverfew herb, astragalus root, Red Raspberry leaf; Foti root, Alfalfa herb, Ginger root, Black Cohosh root, Cat's claw root, Nettle root, St John Wort herb, Echinacea Angustifolia root and Red Clover tops.

* * * * *

UNITED STATES PATENT AND TRADEMARK OFFICE
CERTIFICATE OF CORRECTION

PATENT NO. : 6,889,923 B2
DATED : May 10, 2005
INVENTOR(S) : Emilio J. Gutierrez et al.

It is certified that error appears in the above-identified patent and that said Letters Patent is hereby corrected as shown below:

Column 2,
Line 41, insert a period -- . -- between "form" and "In".
Line 64, insert a comma -- , -- between "process" and "and".

Column 4,
Line 56, replace "compresses" with -- compressed --.

Column 7,
Line 58, replace "grow" with -- group --.

Column 8,
Line 18, replace "pro-milling" with -- pre-milling --.
Line 57, replace "firm" with -- form --.

Column 9,
Line 1, replace "trough" with -- through --.
Line 3, replace "tough" with -- through --.
Line 19, replace "o" with -- of --.

Column 10,
Lines 18 and 48, replace "Raspeberry" with -- Raspberry --.
Line 23, replace "Officioslls" with -- Officinalis --.
Line 34, replace "baying" with -- having --.
Line 35, insert a semicolon -- ; -- after "flowablility".
Line 46, replace "purpurca" with -- purpurea --.
Line 51, replace ";" after "leaf" with -- , --.
Line 56, replace "St John" with -- St. John --.

Signed and Sealed this

Twenty-first Day of February, 2006

JON W. DUDAS
*Director of the United States Patent and Trademark Office*